US 6,623,427 B2

(12) United States Patent
Mandigo

(10) Patent No.: US 6,623,427 B2
(45) Date of Patent: Sep. 23, 2003

(54) BIOFEEDBACK BASED PERSONAL ENTERTAINMENT SYSTEM

(75) Inventor: Lonnie D Mandigo, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 09/963,187

(22) Filed: Sep. 25, 2001

(65) Prior Publication Data
US 2003/0060728 A1 Mar. 27, 2003

(51) Int. Cl.[7] .............................. A61B 5/00; A61B 5/04; A61B 5/05; A61B 5/02; A61B 5/08
(52) U.S. Cl. .................... 600/300; 600/545; 600/544; 600/346; 600/481; 600/529; 600/546
(58) Field of Search .................. 600/544, 545, 600/300, 301, 346, 481, 529, 508, 485, 483, 546

(56) References Cited
U.S. PATENT DOCUMENTS

| 3,855,998 A | * 12/1974 | Hidalgo-Briceno | 600/545 |
|---|---|---|---|
| 5,875,108 A | 2/1999 | Hoffberg et al. | 364/146 |
| 6,001,065 A | 12/1999 | DeVito | 600/544 |
| 6,078,829 A | 6/2000 | Uchida et al. | 600/310 |
| 6,166,496 A | 12/2000 | Lys et al. | 315/316 |
| 6,172,941 B1 | 1/2001 | Bieramperl | 368/10 |
| 6,230,192 B1 | 5/2001 | Roberts et al. | 709/217 |
| 6,230,207 B1 | 5/2001 | Roberts et al. | 709/236 |

* cited by examiner

Primary Examiner—Max F. Hindenburg
Assistant Examiner—Navin Natnithitadha

(57) ABSTRACT

A personal entertainment system calibrated and controlled by the biological or physiological condition of a user is disclosed. The entertainment system includes a media player; a sensor operative to detect biological parameters and generating a control signal in response to the detected parameters, the sensor being operably coupled to the media player; and a processing element which associates the control signal to at least one type of media preference, and causes the media player to provide media stimuli based on the control signal. Thus the media stimuli provided by the entertainment system is specific to the individual preferences and detected condition of the user.

21 Claims, 5 Drawing Sheets

FIG.3

| PIECE | PHYSIOLOGICAL STATE | CATEGORY |
|---|---|---|
| JAZZ | X | PEACEFUL |
| ROCK | Y | ENERGIZED |
| INSTRUMENTAL | Z | SLEEPY |

| MUSICAL PIECE | PHYSIOLOGICAL STATE | CATEGORY | USER |
|---|---|---|---|
| JAZZ | X | PEACEFUL | A |
| FUSION | X | PEACEFUL | B |
| ROCK | Y | ENERGIZED | A |
| INSTRUMENTAL | Z | SLEEPY | A |

72  74  76  78

US 6,623,427 B2

BIOFEEDBACK BASED PERSONAL ENTERTAINMENT SYSTEM

FIELD OF THE INVENTION

The present invention generally relates to personal entertainment systems and, more particularly, to a system and corresponding method for selecting and providing music and other entertainment products to a user based on biological responses of the user.

BACKGROUND OF THE INVENTION

Musical preferences vary based on individual taste as well as a person's mood. The type (or genre) of music listened to will frequently vary with the listener's mood. For example, when a person feels like dancing, they might want to listen to music that has a beat or rhythm. When a person is feeling sad, they may want to hear blues, etc. Also, when a person wants to obtain a certain mood, or emotional state, they may want to listen to a particular type of music. For example, when a person wants to feel energetic, they may want to listen to rock music, etc. Music can control how a person acts or feels. A person's mood or state of mind can frequently be inferred from readily measurable physiological conditions, such as pulse, blood pressure, temperature and brain wave activity.

Presently, when a person wants to listen to a particular type or piece of music, they have to manually place a media storage device (e.g. compact disc, tape, record) onto a media player and then start the media player before they can listen to any music. Also, if a person wants to hear music from a variety of genres or artists, they will have to manually place several media storage devices onto the media player at different times in order to hear the variety they want. Depending on the mood of the person, or the situation the person is in, this can be an aggravating process. For example, if a person originally listening to blues selections wants to listen to a different type of music (e.g. jazz), they will have to manually stop the playing of the blues music; manually select the jazz selection; and play the new musical selection. If, for whatever reason, the user doesn't like the new jazz selection, the process of changing the music selection has to be repeated. The continual manual selection and playing of several music genres can become time consuming.

Thus, there is presently a need for a system and method for automatically selecting and playing music or other media selections based on the individual moods, emotions, or preferences of a user.

SUMMARY OF THE INVENTION

Broadly stated, the present invention is directed to a personal entertainment system that is programmed and calibrated by the biological response of a user based, at least in part, on media stimuli provided to the user. In an exemplary embodiment the stimuli provided to the user is music. Based on the persons physiological state (i.e. mood), after hearing a music selection, a user preference table is generated associating or correlating the physiological state of the user with respect to the music provided to the user. In this fashion, the entertainment system will only play the music preferred by the user in response to the detected physiological state of the user.

In application, the personal entertainment system comprises a media player; a sensor operative to detect biological parameters and generating a control signal in response to the detected parameters, the sensor being operably coupled to the media player; and a processing element which associates the control signal to at least one type of media preference, and causes the media player to provide media stimuli based on the control signal.

BRIEF DESCRIPTION OF THE DRAWINGS

The advantages and features of the present invention will become apparent upon review of the following detailed description of the invention, taken in conjunction with the following drawings, where like numerals represent like elements, in which:

FIG. 3 is an illustration of the table generated by the processing subsystem of FIG. 2 providing the correspondence between physiological state and media stimuli;

FIG. 7 is an illustration of a multi-user preference table generated by the entertainment system of FIG. 6.

DETAILED DESCRIPTION OF THE PREFERRED EMBODIMENTS

Figure 1:
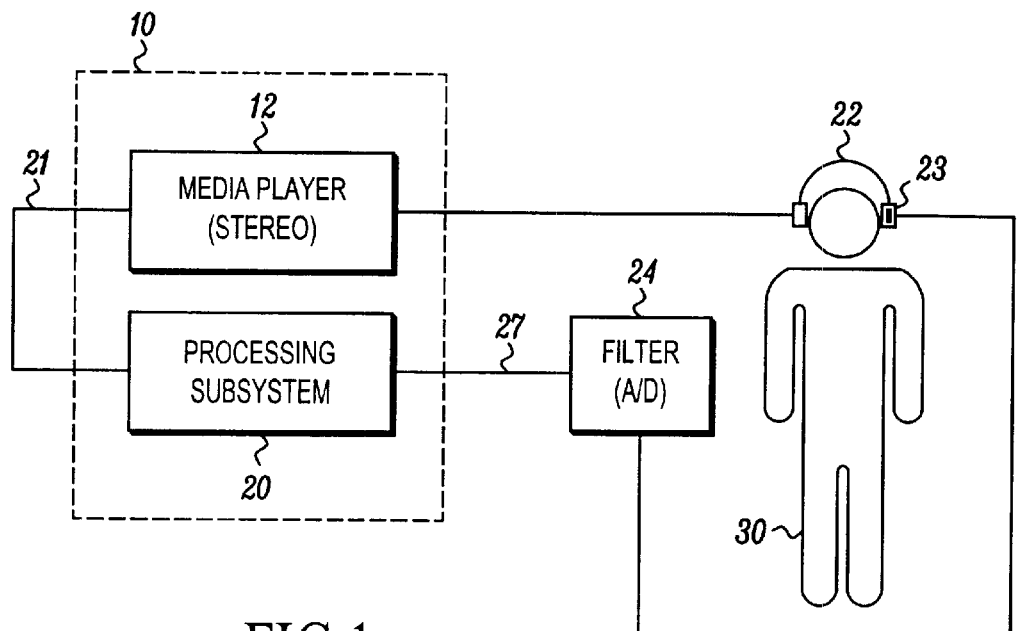
FIG. 1 is a schematic block diagram of an exemplary biofeedback based entertainment system according to the present invention.
Figure 2:
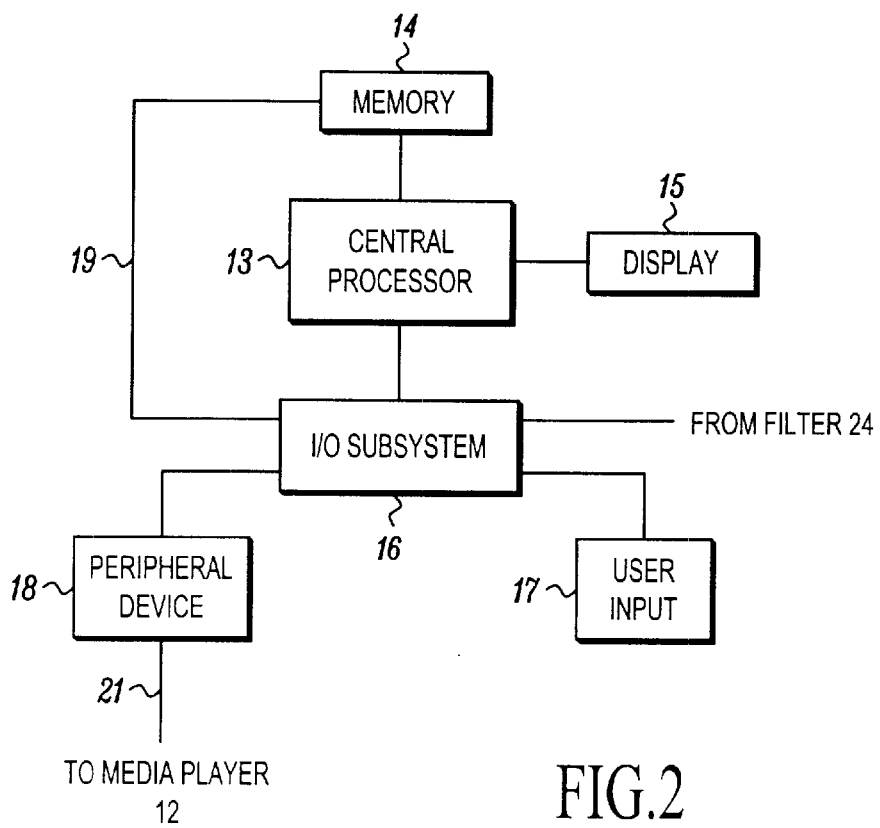
FIG. 2 is a schematic block diagram of the processing subsystem used by the entertainment system of FIG. 1 to monitor and provide the biological or physiological state of the user.

The biofeedback based personal entertainment system of the present invention will now be described with reference to FIGS. 1–7. FIG. 1 is a schematic block diagram of a biofeedback based entertainment system according an exemplary embodiment of the present invention. An advantage provided by the entertainment system of the present invention is that the media selections provided thereby will be tailored to the specific preferences of individual users. Another advantage provided by the entertainment system of the present invention is that it automatically provides the type of music that a user desires without the need for manually changing or selecting music from several sources.

As illustrated in FIG. 1, the entertainment system 10 includes a media player 12 and a processing element or subsystem 20. The media player 12 can be any device capable of providing audio and/or visual information or stimuli to a user 30. Examples of such devices include a stereo, compact disc (CD) player, record player, audio tape player, video cassette player, video tape player, video game console, etc. In an exemplary embodiment, the media player 12 is a stereo. The stimuli provided by the media player 12 is transmitted to the user 30 via headphones 22. The processing subsystem 20 is coupled to the media player 12 via line 21, and is operative to control the amount and type of stimuli provided by the media player 12 based on the physiological or emotional state of the user 30. The structure and operation of the processing subsystem 20 will be described in greater detail below with reference to FIGS. 2 and 3.

Headphones 22 (preferably), include therein one or more sensors 23 adapted to detect a biological or physiological state of the user 30. Examples of such detectable states include, but are not limited to: heart rate, respiration, perspiration, alpha waves, blood pressure, pulse and muscle contractions. Other detectable states will be appreciated by those of ordinary skill in the art. The aforementioned measurable or detectable states can be used to quantify and identify the physical and/or emotional state of the user.

The detected physiological state is appropriately filtered and converted into a suitable format by filter 24 before being transmitted on line 27 to the processing subsystem 20 for analysis and processing. The type of filter employed depends, at least in part, on the type of information being detected by the sensor 23. For example, if the sensor 23 is detecting the user's blood pressure, then filter 24 would include a blood pressure cuff. If alpha waves or the electrical activity of the user's brain is being sensed, then filter 24 would include an electroencephalograph (EEG). Similarly, if temperature is considered indicative of a mood or state of mind, a thermocouple or other temperature sensor is used and its output appropriately filters. In any case, filter 24 includes an analog-to-digital (A/D) converter, which digitizes the filtered data before such filtered data is analyzed by the processing element 20.

Briefly stated, the entertainment system 10 of FIG. 1 operates as follows: audio information provided by stereo 12 is provided to the user 30, preferably via headphones 22. A physiological state (e.g., pulse, blood pressure, temperature or EKG) is detected by sensor 23 and converted into an appropriate digital signal by filter 24. The digital representation of the user's physiological state is then transmitted to the processing subsystem 20. Within the processing subsystem, a preference table is generated which is used to correlate the type or genre of music being provided by the stereo 12 with the resulting physiological state detected by sensor 23. The user is then prompted by the processor to enter an identifier, which will be used as an index to the preference table. Different types of music are played to the user, wherein the physiological state of the user is automatically detected or sensed and stored within the preference table. The user then provides an identifier for the state which the user is in. For example, if jazz music is being provided by the stereo, the user may identify the physiological state which is measured by sensor 23 as being peaceful. In one instance the preference table under an entry "peaceful" would contain the genre jazz and the particular physiological state as measured by the sensor. Such information is then used at subsequent times to automatically play the piece(s) or genre of music appropriate to the individual user based on the detected physiological state of the user by the sensor 23, or user input.

In addition to using headphones, audio loud speakers can be used to reproduce music. In addition to playing music, the system might also play video images. In instances where loud speakers are used to reproduce recorded music and video is played, physiological sensors need to be attached to the subject appropriately and not necessarily party of the headphones as described hereinafter.

The processing subsystem 20 (FIG. 2) includes a central processor 13, a memory 14, display driver 15, and I/O subsystem 16. The aforementioned components are interconnected and connected to the central processor 13 via system bus 19. The I/O subsystem 16 is used to couple user information provided at input 17 to the processor 13. Also, the I/O subsystem 16 is used to send music and other control information to the media player 12 via peripheral device driver 18. The digital information provided by the filter 24 is also provided to the central processor 13 via the I/O subsystem 16.

The memory 14 of the processing subsystem 20 contains musical selections and a searchable preference table (FIG. 3) containing three columns. The first column is labeled "PIECE", which relates to the individual song or genre of music provided to the user. The second column is labeled "PHYSIOLOGICAL STATE" and contains the measured physiological state (e.g., pulse) of the user while listening to a particular type of music identified under the "PIECE" column. The third column is labeled "CATEGORY" and is used to store the user-defined identifier which describes the state the user is in when listening to the corresponding musical piece (PIECE). For example, as illustrated in FIG. 3, jazz pieces are indicated as placing the user in a peaceful mood. The peaceful state corresponds to a pulse rate (i.e., measured physiological state) of X. Rock music is indexed by the label "energized", and corresponds to a measured physiological state of Y. Additionally, instrumental music has been identified as making the user feel tired or sleepy, and corresponds to a measured physiological state Z. The entries of this preference table can contain information relating to any individual or group of music genres and a corresponding physiological state, or mood, that such music places the user in. It is to be noted that the identifier given to the particular piece or genre of music is modifiable by the user.

The user-defined identifiers given to the preference table entries are entered into the processing subsystem 20 via the user input 17. Visual indication of the entries being made by the user is provided on a suitable display via display driver 15. Examples of the display would be a CRT, computer monitor, touch screen, etc.

The entertainment system 10 operates principally two modes: (1) a calibration or training mode, where the association between a musical genre and the physiological state of the user is determined and indexed; and (2) a user or playback mode, where audio and/or video information is provided to the user based on the measured or inputted physiological state of the user.

Figure 4:
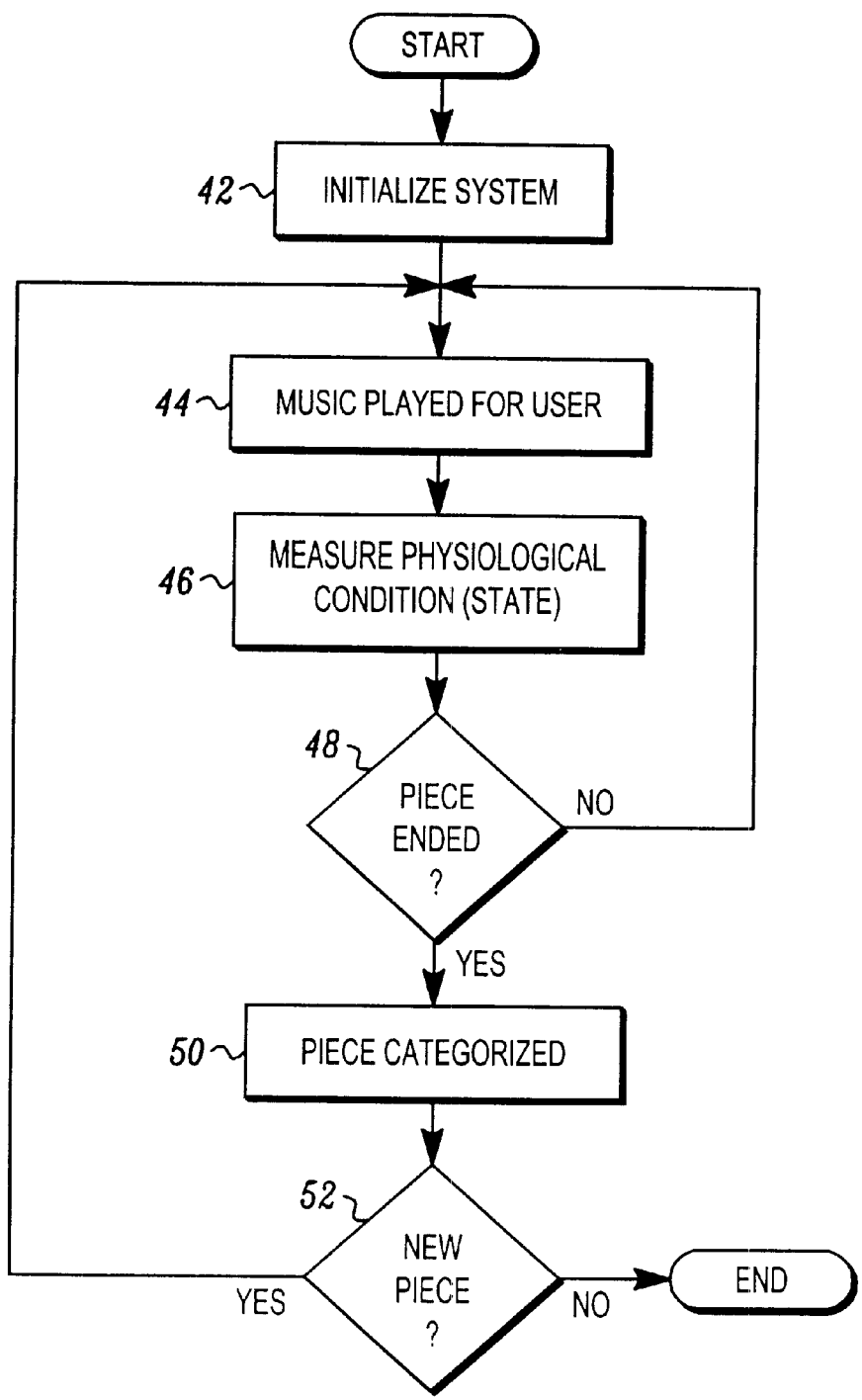
FIG. 4 is a flow chart illustrating the operating steps performed by the entertainment system of the present invention during the calibration phase.
Figure 5:
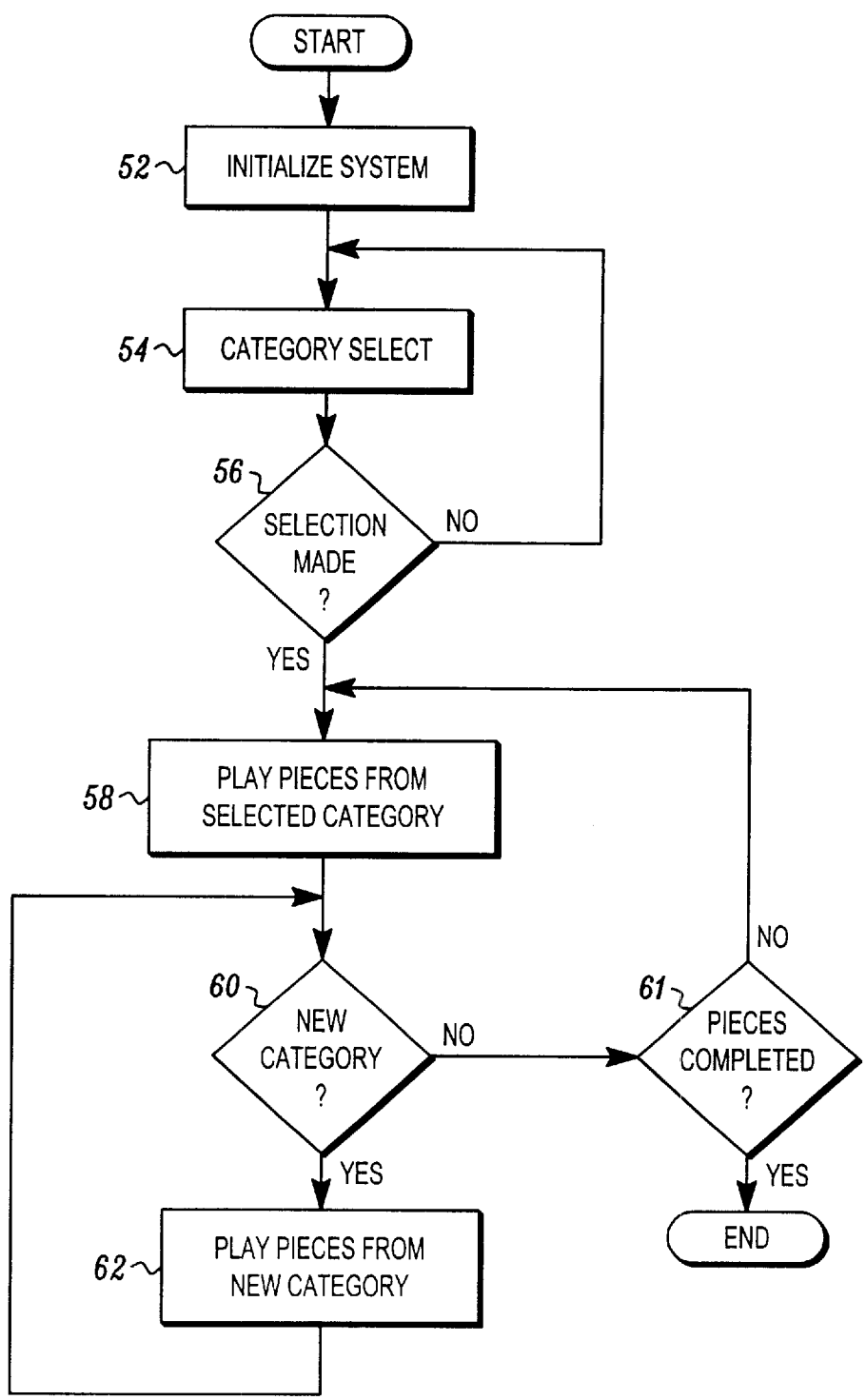
FIG. 5 is a flow chart illustrating the operating steps performed by the entertainment system of the present invention during the user or playback phase.

As illustrated in FIG. 4, the calibration or training mode of the entertainment system begins at step 42 where the entertainment system is initialized, typically by zeroing out. Next, (step 44) music from a particular artist or genre is provided by subsystem 20 and played for the user. In step 46, while listening to the selected music piece, the sensor 23 measures a physiological state (e.g., pulse) of the user. This measured physiological state is then appropriately filtered by filter 24 and then transmitted to the processor where the measured state parameter is placed in the corresponding column in the preference table (FIG. 3). In step 48, a determination is made as to whether the musical piece has ended. If the piece has not ended, play continues in conjunction with the continued measurement of the user's physiological state.

On the other hand, if the piece has ended, the user is prompted by the central processor 13 to enter an identifier, in step 50, which describes the physiological state that the user is in. This user-defined identifier is then placed in the third column of the preferences table (FIG. 3). Next, in step 52, a determination is made as to whether a subsequent piece is going to be played for the user. If a new piece is going to be played, the process moves back to step 44 where the musical piece is played for the user. If no further musical pieces are to be played, the calibration mode ends.

At the end of the calibration mode, each row of the preferences table (FIG. 3) includes an identification of the type or piece of music played, the measured physiological state of the user attained while listening to the musical piece(s), and a identifier which describes the physiological state of the user. This preferences table can then be used in the user or playback mode to automatically provide a specific type of music to the user in response to either user entered information or the measured physiological state of the user. The user or playback mode will now be described with reference to FIG. 5.

The playback mode begins at step 52, with the initialization of the entertainment system. Next, the central processor 13 (FIG. 2) prompts the user to enter in the particular physiological state that the user would like to obtain in step 54. In step 56, a determination is made as to whether the user has selected a desired physiological state. If no selection has been made, the system waits a user-programmable length of time until a selection is made and if no selection has been made, the system turns itself off. On the other hand if a selection is made, the system then moves to step 58 where the musical piece(s) corresponding to the selected category are played for the user. Next, in step 60, a determination is made as to whether the user has selected a new category. If no new category has been entered, the process moves to step 61 where a determination is made as to whether the music pieces from the category selected in step 54 have been played. If the pieces from the original selected category have all been played, the process ends. On the other hand, if the pieces from the original selected category have not all been played, the process moves to step 58 where the playing of the music from such musical category continues.

If the user has selected a new music category (representing a new physiological state) in step 60, the process shifts to step 62 where the processor sends a signal to the media player via line 21, resulting in the media player 12 playing music from the newly selected category. The music from the newly selected category (step 60) continues to play until either the user selects a new category or the pieces from the category are completed. Upon completion of the playing of the musical pieces, the physiological state as measured by the sensor 23 (FIG. 1), should be in the range provided in the preferences table.

Thus, the aforementioned biofeedback based entertainment system provides for the user only listening to the particular type of music or music genre that the user prefers to listen to either based on actual input provided by the user, or the present physiological condition of the user as measured by the sensor. In this fashion, the user does not have to manually handle and interchange several music storage elements (e.g., CDs or tapes) in order to listen to the selection of music that the user prefers at any given time. This provides for a more enjoyable music experience.

Although the biofeedback based entertainment system was described as having the sensor, which detects the physiological state of the user, being contained within the headphones 22, the sensor is not limited to that particular embodiment. Alternatively, the sensor device can be maintained on or within a mouse, which can be connected to the processing subsystem 20 via user input 17. A bracelet can be used in lieu of the headphones 22 for measuring physiological state such as the pulse or heart rate of the user. Additionally, digit sensors, or a sensor placed on the fingers or toes of the user can also be used. All that is required is that the corresponding sensor is able to detect the physiological state of the user.

Figure 6:
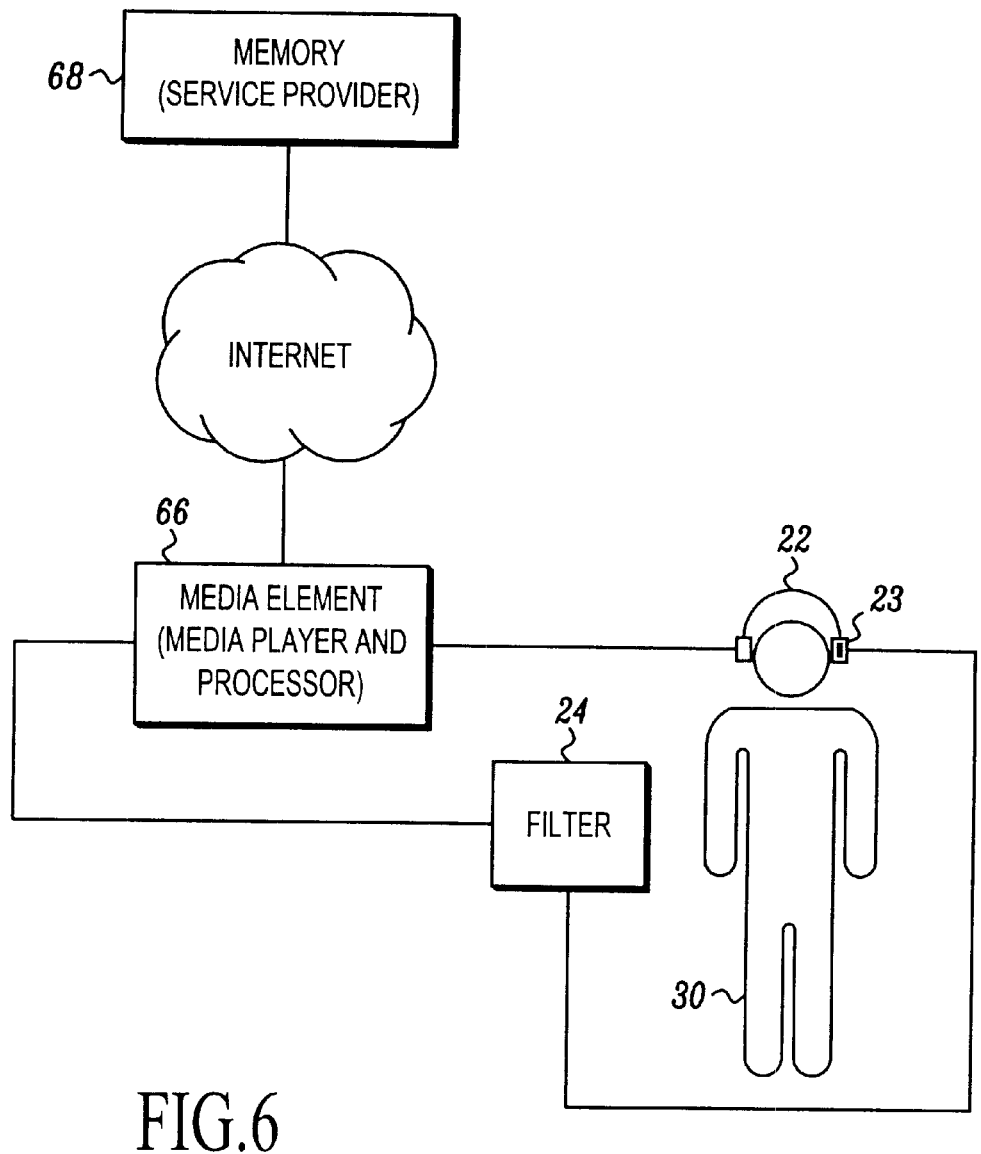
FIG. 6 is a schematic block diagram of an alternative biofeedback based entertainment system according to the present invention.

An alternate embodiment of the present invention utilizing a service provider which maintains the preference table is illustrated in FIG. 6. As shown in FIG. 6, the preference table is maintained in a memory 68 which is stored in a location remote from the media element 66. For example, the memory 68 which contains the preferences table (FIG. 7) is maintained at a service provider's location. The media player and the components used to measure, or detect, the physiological state of the user is maintained at the user's location within media element 66. When the user wants to enter a particular mode, or wants to listen to music of a particular genre or genres, the user places the headphones 22 upon their person, wherein the corresponding sensor 23 detects the physiological state of the user. The detected physiological state of the user 30 is appropriately filtered by filter 24 and then transmitted to the media element 66. Upon being received by the media element, a signal is sent to the service provider via, for example, the Internet 70. Upon receiving the physiological state information from the user 30, the user's individual preferences table is accessed and based on the received physiological state, the corresponding music genre or selected pieces of music will be provided to the user. In application, the service provider receives the physiological state information via a communication link (i.e., Internet 70). The genre of music indexed by the particular physiological state information is then provided by communication link 70 to the media element 66, thereby causing the media player to play the music corresponding to the received physiological state.

In an alternate embodiment, the user 30 may enter the identifier of the physiological state that they wish to enter into the media element 66 that user-defined information is then passed to the service provider memory 68 via the communication link 70. The particular genre or pieces of music corresponding to the entered category is then transmitted to the media player (contained within conduit 66) via the communication link, thereby causing the media player to play the corresponding music to the user.

In addition to maintaining the preferences table to the individual user 30, the provider of memory 68 also has the ability to store and manipulate data based on a number of users. As illustrated in greater detail in FIG. 7, an example of an aggregate preference table maintained by the service provider at memory 68 is shown. As illustrated in FIG. 7, the aggregate preferences table includes four columns: (1) musical piece or genre 70; (2) physiological state 72; (3) user-defined category 74; and (4) protected identification of the particular user 76. To avoid privacy issues, the names of the individual users are not provided in or indexed by the table. Instead, an encrypted or other non-public identifier is used to identify the individual user. The advantage of providing this aggregated preference table is that user A may have identified a category containing physiological (measured) state information substantially equal or identical to that of user B; however, the particular musical pieces or genre(s) may not be identical for users A and B. Thus, the service provider may provide the additional benefit of distributing additional music to user A, which may place user A in the desired physiological state. In similar fashion, the service provider may provide user B with the musical pieces stored in user A's category (without identifying either user to one another) thereby placing user B in the requested or measured physiological state. Thus, the biofeedback based entertainment system of the present invention provides for an expansive capability that can be readily modified based on individual user(s) preferences.

The above detailed description of the invention and the examples described herein have been provided for the purposes of illustration and description. It is therefore contemplated to cover by the present invention, any and all modifications, variations or equivalents that fall within the spirit and scope of the basic underlying principles disclosed and claimed herein.

What is claimed is:

1. A personal entertainment system, comprising:

a media player;

a sensor operative to detect biological parameters of a user and generating a control signal in response to the detected parameters, the sensor being operably coupled to the media player; and a processing element which associates the control signal to at least one type of media preference according to a user preference table that cross-references the detected biological parameters with the user's mood rind at least one type of media preference; and causes the media player to provide media stimuli based on the control signal.

2. The entertainment system of claim 1, wherein the control signal is modifiable such that the media stimuli provided by the media player is configured based at least in part on the modifiable control signal.

3. The entertainment system of claim 2, wherein the media player is controlled by the modifiable control signal and the modifiable control signal can be modified to indicate a target biological parameter.

4. The entertainment system of claim 3, wherein the biological parameter is a measurable physical state comprising: heart rate, pulse, perspiration, blood pressure, alpha waves, muscle contractions and respiration.

5. The entertainment system of claim 1, wherein the media player and the processing element are remote from the sensor and further including means for remotely linking the sensor, media player and processing element.

6. The entertainment system of claim 1, wherein the media stimuli provided by the media player includes at least one member selected from a group comprising: audio information and video information.

7. The entertainment system of claim 1, wherein the sensor further includes a filtering element operative to convert the detected biological parameter into a processor readable signal.

8. The entertainment system of claim 1, further including a storage element for maintaining a media play list indexed by the control signal.

9. The entertainment system of claim 1, wherein the media player provides entertainment pieces from a play list to a user in response to the control signal, the play list corresponding to and being indexed by the control signal.

10. The apparatus of claim 1 wherein the user's mood in the user preference table is determined in advance and entered into the user preference table by the user calibrating the personal entertainment system.

11. The apparatus of claim 10 wherein the user calibrating is performed using a calibration component comprising:

a media player that provides stimuli to the user;

at least one sensor that measures the physiological state of the user as the media player provides stimuli to the user; and a user input component prompting the user to enter an identifier that describes the user's mood while receiving the media stimuli.

12. The apparatus of claim 1 wherein the user's mood in the user preference table is calibrated and populated based on information in an aggregated preferences table that cross-references and aggregates the self-identified moods of many users with one or more types of media stimuli preferences.

13. The apparatus of claim 12 wherein the aggregated preferences table is maintained by a service provider connected over a communication link to the personal entertainment system wherein the service provider gathers private information from the many users in addition to a user's self-identified mood and corresponding one or more type of media stimuli preferences.

14. A method of operating a personal entertainment system, comprising:

monitoring a user;

detecting measurable physiological conditions of the user in response to media stimuli and converting the detected conditions into a control signal, the control signal representing the physiological condition of the user;

associating the control signal with at least one type of media stimuli preference according to a user preference table that cross-references the detected biological parameters with an identifier for the user's mood and at least one type of media stimuli preference; and providing the user with media stimuli in response to the control signal.

15. The method of claim 14, wherein the associating step includes:

storing the media stimuli; and indexing the stored media stimuli by the control signal.

16. The method of claim 15, wherein the storing step further includes:

storing the media stimuli in a table and further storing a user defined value representing the physiological condition caused by the presentation of the media stimuli, the user defined value being used as an index to the table.

17. The method of claim 14, wherein the identifier for the user's mood is modifiable based at least in part on the type of media stimuli provided to the user.

18. The method of claim 14 wherein the user's mood in the user preference table is determined in advance and entered into the user preference table by the user calibrating the personal entertainment system.

19. The method of claim 18 wherein the user calibrating further comprises:

providing media stimuli to the user;

measuring the physiological state of the user as the selected media stimuli is provided to the user; and prompting the user to enter an identifier that describes the user's mood while receiving the media stimuli.

20. The method of claim 14 wherein the user's mood in the user preference table is calibrated and populated based on information in an aggregated preferences table that cross-references and aggregates the self-identified moods of many users with one or more types of media stimuli preferences.

21. The method of claim 20 wherein the aggregated preferences table gathers private information from the many users in addition to a user's self-identified mood and corresponding one or more type of media stimuli preferences.

* * * * *

UNITED STATES PATENT AND TRADEMARK OFFICE
CERTIFICATE OF CORRECTION

PATENT NO. : 6,623,427 B2 Page 1 of 1
DATED : September 23, 2003
INVENTOR(S) : Mandigo It is certified that error appears in the above-identified patent and that said Letters Patent is hereby corrected as shown below:

<u>Column 7,</u>
Line 16, delete "rind" and insert therefor -- and --.
Line 17, delete "preference;" and insert therefor -- preference --.

Signed and Sealed this

Fifteenth Day of June, 2004

JON W. DUDAS
*Acting Director of the United States Patent and Trademark Office*